(12) United States Patent
Blommel et al.

(10) Patent No.: US 9,873,644 B2
(45) Date of Patent: *Jan. 23, 2018

(54) HYDROGENATION OF CARBOXYLIC ACIDS TO INCREASE YIELD OF AROMATICS

(71) Applicant: Virent, Inc., Madison, WI (US)

(72) Inventors: Paul Blommel, Oregon, WI (US); Randy Cortright, Madison, WI (US)

(73) Assignee: Virent, Inc., Madison, WI (US)

(*) Notice: Subject to any disclaimer, the term of this patent is extended or adjusted under 35 U.S.C. 154(b) by 123 days.

This patent is subject to a terminal disclaimer.

(21) Appl. No.: 14/284,999

(22) Filed: May 22, 2014

(65) Prior Publication Data

US 2014/0350317 A1 Nov. 27, 2014

Related U.S. Application Data

(60) Provisional application No. 61/826,163, filed on May 22, 2013.

(51) Int. Cl.
| | |
|---|---|
| *C07C 1/207* | (2006.01) |
| *C07C 1/24* | (2006.01) |
| *C10G 3/00* | (2006.01) |
| *C07C 1/20* | (2006.01) |

(52) U.S. Cl.
CPC ............... *C07C 1/24* (2013.01); *C07C 1/20* (2013.01); *C07C 1/2072* (2013.01); *C10G 3/49* (2013.01); *C10G 3/50* (2013.01); *C07C 2521/04* (2013.01); *C07C 2529/24* (2013.01); *C10G 2400/30* (2013.01); *Y02P 30/20* (2015.11)

(58) Field of Classification Search
None
See application file for complete search history.

(56) References Cited

U.S. PATENT DOCUMENTS

| | | | |
|---|---|---|---|
| 1,526,461 | A | 2/1925 | Cram |
| 3,702,886 | A | 11/1972 | Argauer et al. |
| 3,709,979 | A | 1/1973 | Chu |
| 4,076,842 | A | 2/1974 | Plank et al. |
| 3,832,449 | A | 8/1974 | Rosinski et al. |
| 3,894,103 | A | 7/1975 | Chang |
| 3,894,104 | A | 7/1975 | Chang |
| 3,894,105 | A | 7/1975 | Chang |

(Continued)

FOREIGN PATENT DOCUMENTS

| | | |
|---|---|---|
| GB | 1446522 | 8/1976 |
| GB | 1526461 | 9/1978 |

(Continued)

OTHER PUBLICATIONS

Chen, N. Y., et al. "Fluidized-bed upgrading of wood pyrolysis liquids and related compounds." 1988. 277-289.

(Continued)

*Primary Examiner* — Philip Louie
(74) *Attorney, Agent, or Firm* — Quarles & Brady LLP

(57) ABSTRACT

The present invention provides methods, reactor systems, and catalysts for increasing the yield of aromatic hydrocarbons produced while converting carboxylic acids to aromatic hydrocarbons. The invention includes methods of using catalysts to increase the yield of benzene, toluene, and mixed xylenes in the hydrocarbon product.

16 Claims, 4 Drawing Sheets

(56) References Cited

U.S. PATENT DOCUMENTS

| | | | |
|---|---|---|---|
| 3,894,106 | A | 7/1975 | Chang |
| 3,907,915 | A | 9/1975 | Chang |
| 3,998,898 | A | 12/1976 | Chang |
| 4,016,245 | A | 4/1977 | Plank et al. |
| 4,039,600 | A | 8/1977 | Chang |
| 4,076,761 | A | 2/1978 | Chang |
| 4,100,262 | A | 7/1978 | Pelrine |
| 4,107,195 | A | 8/1978 | Rollmann |
| 4,139,600 | A | 2/1979 | Rollmann et al. |
| 4,359,587 | A | 11/1982 | Abdurakhmanov |
| 4,375,573 | A | 3/1983 | Young |
| 5,019,663 | A | 5/1991 | Chou et al. |
| 7,022,888 | B2 | 4/2006 | Choudhary et al. |
| 7,767,867 | B2 | 8/2010 | Cortright |
| 7,977,517 | B2 | 7/2011 | Cortright et al. |
| 8,017,818 | B2 | 9/2011 | Cortright et al. |
| 8,053,615 | B2 | 11/2011 | Cortright et al. |
| 2008/0216391 | A1 | 9/2008 | Cortright |
| 2010/0077655 | A1* | 4/2010 | Bauldreay ........ C10L 1/04 44/437 |
| 2010/0197959 | A1* | 8/2010 | Johnston ........ C07C 67/00 560/265 |
| 2013/0131411 | A1 | 5/2013 | Blommel et al. |

FOREIGN PATENT DOCUMENTS

| | | |
|---|---|---|
| JP | 50-076027 | 6/1975 |
| JP | 52-008005 | 1/1977 |
| JP | 57-102835 | 6/1982 |
| WO | 2012162403 A1 | 11/2012 |

OTHER PUBLICATIONS

Chen, N. Y., et al. "Liquid fuel from carbohydrates." Chemtech 16.8 (1986): 506-511.

Fuhse, Jürgen, et al. "Conversion of organic oxygen compounds and their mixtures on H-ZSM-5." Chemical engineering & technology 10.1 (1987): 323-329.

Zhang, Huiyan, et al. "Catalytic conversion of biomass-derived feedstocks into olefins and aromatics with ZSM-5: the hydrogen to carbon effective ratio." Energy & Environmental Science 4.6 (2011): 2297-2307.

* cited by examiner

HYDROGENATION OF CARBOXYLIC ACIDS TO INCREASE YIELD OF AROMATICS

CROSS-REFERENCE TO RELATED APPLICATIONS

This application claims benefit of U.S. Provisional Application Ser. No. 61/826,163 filed on May 22, 2013, which is incorporated by reference herein in its entirety.

TECHNICAL FIELD

The present invention is directed to catalysts and methods for producing aromatic hydrocarbons from carboxylic acids at high yields.

BACKGROUND OF THE INVENTION

Aromatic hydrocarbons, notably benzene, toluene, and xylenes are important industrial commodities used to produce numerous chemicals, fibers, plastics, and polymers, including styrene, phenol, aniline, polyester, and nylon. Typically, such aromatic hydrocarbons are produced from petroleum feedstocks using well-established refining or chemical processes. More recently, there is a growing interest in providing aromatic hydrocarbons from alternative resources, such as biomass, synthesis gas and natural gas.

One possible resource is plant biomass. Plant biomass is the most abundant source of carbohydrate in the world due to the lignocellulosic materials composing the cell walls in higher plants. Plant cell walls are divided into two sections, primary cell walls and secondary cell walls. The primary cell wall provides structure for expanding cells and is composed of three major polysaccharides (cellulose, pectin, and hemicellulose) and one group of glycoproteins. The secondary cell wall, which is produced after the cell has finished growing, also contains polysaccharides and is strengthened through polymeric lignin covalently cross-linked to hemicellulose.

The resulting composition of the biomass provides roughly 40-50% cellulose, 20-25% hemicellulose, and 25-35% lignin, by weight percent. Cellulose is typically the primary sugar source for bioconversion processes and includes high molecular weight polymers formed of tightly linked glucose monomers. Hemicellulose is generally considered a secondary sugar source and includes shorter polymers formed of various sugars. Lignin includes phenylpropanoic acid moieties polymerized in a complex three dimensional structure and is often viewed as a waste material or byproduct useful for other processes. Collectively, the components of cellulose, hemicellulose, and lignin are often referred to as oxygenated hydrocarbons.

Heterogeneous catalysts have shown great promise for converting biomass-derived oxygenated hydrocarbons into fuels and chemicals. A difficult challenge to overcome is obtaining high yields of select hydrocarbons while minimizing coke formation and catalyst deactivation.

Chen et al. developed the hydrogen to carbon effective ($H:C_{eff}$) ratio as a tool to assist in determining the suitability of oxygenated hydrocarbon feedstocks for catalytic conversion to hydrocarbons using zeolite catalysts (N. Y. Chen, J. T. F. Degnan and L. R. Koeing, Chem. Tech. 1986, 16, 506). The $H:C_{eff}$ ratio is based on the amount of carbon, oxygen and hydrogen in the feed, and is calculated as follows:

$$H:C_{eff} = \frac{H - 2O}{C} \quad \text{(equation 1)}$$

where H represents the number of hydrogen atoms, O represents the number of oxygen atoms, and C represents the number of carbon atoms. Water and molecular hydrogen (diatomic hydrogen, $H_2$) are excluded from the calculation. The $H:C_{eff}$ ratio applies both to individual components and to mixtures of components, but is not valid for components which contain atoms other than carbon, hydrogen, and oxygen. For mixtures, the carbon, hydrogen, and oxygen atoms are summed over all components exclusive of water and molecular hydrogen. The term "hydrogen" refers to any hydrogen atom while the term "molecular hydrogen" is limited to diatomic hydrogen, $H_2$.

Zhang et al. studied the impact of the $H:C_{eff}$ ratio on the conversion of various biomass-derived oxygenated hydrocarbons to coke, olefins and aromatics using a ZSM-5 catalyst (Zhang et al., Catalytic conversion of biomass-derived feedstocks into olefins and aromatics with ZSM-5: the hydrogen to carbon effective ratio, Energy Environ. Sci., 2011, 4, 2297). Zhang reported that biomass derived feedstocks having $H:C_{eff}$ ratios of between 0 and 0.3 produced high levels of coke, making it non-economical to convert such feedstocks to aromatics and chemicals. However, by hydroprocessing the feedstock to add hydrogen, Zhang was able to produce aromatics and olefins using a ZSM-5 catalyst at yields 2 to 3 times higher than a process without hydrogenation. Specifically, Zhang reported that the aromatic and olefin yields increased from 12% to 24% and 15% to 56%, respectively, with increasing $H:C_{eff}$ ratio. The ratio of olefins to aromatics also increased with increasing $H:C_{eff}$ ratio, with the olefin yield higher than the yield of aromatics for all feedstocks. It was also reported that there is an inflection point at a $H:C_{eff}$ ratio of 1.2, where the aromatic and olefin yield does not increase further, indicating that at most the yield of high value aromatic chemicals, such as benzene, toluene, and xylenes (BTX), may be limited to 24% when using zeolite catalysts according to the Zhang process.

In another study by Fuhse and Bandermann, the researchers studied the conversion of a number of different types of oxygenates over a ZSM-5 catalyst to aromatic hydrocarbons (Fuhse and Bandermann, Conversion of Organic Oxygen Compounds and their Mixtures on H-ZSM-5, Chem. Eng. Technol., 1987, 10, 323-329). The researchers reported oxygenates having $H:C_{eff}$ ratios less than 1.6 cause the problem of coking, decreasing the catalyst's lifetime. The researchers also report that conversion of carboxylic acids and esters cannot be explained solely by the $H:C_{eff}$ ratio because these types of reactants undergo the side reactions of decarbonylation, decarboxylation, and ester pyrolysis. For example, the researchers reported that the reaction of acetic acid yields only acetone and $CO_2$. Moreover, when the researchers investigated mixtures, the researchers stated that the conversion of mixtures to products depends on the individual components, and that when oxygenates having a $H:C_{eff}$ less than 1.6 are added to the mixture the yield of aromatic hydrocarbons decreases.

Because of the low hydrogen to carbon effective ratio of carboxylic acid feedstocks and the likelihood of side reactions, conventional wisdom teaches that these feedstocks are unsuitable for conversion to aromatic hydrocarbons in high yields. As a result, there exists a need for methods and systems to effectively and efficiently convert carboxylic acid feedstocks to aromatic hydrocarbons.

SUMMARY OF THE INVENTION

The invention provides methods for converting carboxylic acids to aromatic hydrocarbons. The method generally involves: (1) exposing a carboxylic acid feedstock to hydrogen and a hydrogenation catalyst at a hydrogenation temperature and a hydrogenation pressure to produce an oxygenate mixture having an $H:C_{eff}$ ratio of between 0.8 and 1.8;

and (2) exposing the oxygenate mixture to a condensation catalyst to produce aromatic hydrocarbons.

One aspect of the invention is that the oxygenate mixture has a desired hydrogen to carbon effective ratio ($H:C_{eff}$ ratio) of between 0.8 and 1.8, or between 1.0 and 1.8, between 1.05 and 1.75, between 1.1 and 1.7, between 1.15 and 1.65, or between 1.2 and 1.6. In one embodiment, the oxygenate mixture has a hydrogen to carbon effective ratio of less than 1.8, 1.75, 1.7, 1.65, 1.6, 1.55, 1.5, 1.45, or 1.4. In another embodiment, the oxygenate mixture has a hydrogen to carbon effective ratio of greater than 0.8, 0.85, 0.9, 0.95, 1.0, 1.05, 1.1, 1.15, 1.2, 1.25, 1.3, 1.35, 1.4, 1.45, or 1.5.

In another aspect of the invention, the condensation temperature is between about 250° C. and 550° C., between about 300° C. and 500° C., or between about 320° C. and 480° C. The condensation pressure ranges from below atmospheric pressure up to about 1000 psig, from about atmospheric pressure to about 700 psig, or from about 10 psig to about 500 psig. In general, the reaction should be conducted under conditions where the residence time of the hydrogenation products over the condensation catalyst is appropriate to generate the desired aromatic hydrocarbons. For example, the residence time may be established at a weight hourly space velocity (WHSV) of between 0.01 and 30, or between 0.05 and 10, or between 0.1 and 5, or between 1.0 and 4.

When the hydrogenation and condensation steps are complete, some of the carbon from the carboxylic acid feedstock is contained within the aromatic hydrocarbons. In one embodiment, more than 40% of carbon in the carboxylic acid feedstock is contained within the aromatic hydrocarbon product. In another embodiment, more than 45%, or more than 50%, or more than 60%, or more than 70%, of carbon in the carboxylic acid feedstock is contained within the aromatic hydrocarbon product.

Another aspect of the invention is the composition of the carboxylic acid feedstock. In one embodiment the carboxylic acid feedstock is derived from material of recent biological origin such that the age of the compounds, or fractions containing the compounds, is less than 100 years old, preferably less than 40 years old, and more preferably less than 20 years old, as calculated from the carbon 14 concentration of the feedstock. In other embodiments, the carboxylic acid feedstock is derived from base-catalyzed dehydrogenation of alcohols, the hydrolysis of triglycerides, fermentation, Fischer-Tropsch, pyrolysis, aqueous phase reforming or other catalytic conversion processes. Examples of applicable carboxylic acids include, without limitation, lactic acid, acetic acid, propionic acid, butyric acid, and valeric acid.

When the carboxylic acid feedstock is exposed to hydrogen and a hydrogenation catalyst at a hydrogenation temperature and pressure, an oxygenate mixture is produced. In one embodiment, the oxygenate mixture comprises a carboxylic acid, alcohol, ester, aldehyde, ketone, and combinations thereof. In other embodiments, the oxygenate mixture the oxygenate mixture comprises an alcohol; an ester; an alcohol and an ester; an alcohol and a carboxylic acid; an ester and a carboxylic acid; or an alcohol, an ester, and a carboxylic acid. Optionally, the oxygenate mixture may further comprise an aldehyde, a ketone, or both an aldehyde and a ketone. In certain embodiments, the oxygenate mixture comprises a plurality of molecules having a hydrogen to carbon effective ratio less than 1.6. In other embodiments, the oxygenate mixture comprises (i) a portion of unreacted feedstock and (ii) a member selected from the group consisting of alcohol, ester, aldehyde, ketone, and combinations thereof.

The hydrogenation catalyst is capable of hydrogenating carboxylic acids to form an oxygenate mixture having a $H:C_{eff}$ ratio of between 0.8 and 1.8, or between 1.0 and 1.8. In one embodiment, the hydrogenation catalyst includes Fe, Ru, Co, Pt, Pd, Ni, Re, Cu, and alloys or combinations thereof, either alone or with promoters such as Ag, Au, Cr, Zn, Mn, Mg, Ca, Cr, Sn, Bi, Mo, W, B, P, and alloys or combinations thereof. The hydrogenation catalyst may also include any one of several supports, depending on the desired functionality of the catalyst. Such supports may include carbon, silica, alumina, zirconia, titania, vanadia, ceria, silica-aluminate, zeolite, kieselguhr, hydroxyapatite, zinc oxide, chromia, and mixtures thereof.

The hydrogenation reaction is conducted at a temperature and pressure where the thermodynamics are favorable. In one embodiment, the hydrogenation temperature is between about 80° C. and 500° C., and the hydrogenation pressure ranges from atmospheric pressure to about 5000 psig.

The aromatic hydrocarbons are produced by catalytically reacting the oxygenate mixture in the presence of a condensation catalyst at a condensation temperature and a condensation pressure. In one embodiment, the condensation catalyst comprises a zeolite. In another embodiment, the condensation catalyst is ZSM-5. The condensation catalyst may be modified by a material selected from the group consisting of phosphorous, gallium, zinc, nickel, tungsten, and mixtures thereof. The condensation catalyst may also contain a binder selected from the group consisting of alumina, silica, silica-alumina, titania, zirconia, aluminum phosphate, and mixtures thereof.

Another aspect of the invention is a method of producing hydrocarbons by catalytically reacting a carboxylic acid feedstock with a multi-functional hydrogenation/condensation catalyst at a temperature and pressure suitable to produce hydrocarbons. In one embodiment, the multi-functional catalyst includes copper loaded onto silica-bound ZSM-5.

Another aspect of the invention is a method of producing aromatic hydrocarbons comprising the steps or acts of: (1) exposing a feedstock comprising a first oxygenate component to hydrogen and a hydrogenation catalyst at a hydrogenation temperature and a hydrogenation pressure to produce a second oxygenate component, and (2) exposing the second oxygenate component to a condensation catalyst at a condensation temperature and a condensation pressure to produce aromatic hydrocarbons.

Another aspect of the invention is a method of converting acetic acid to aromatic hydrocarbons, the method comprising exposing a feedstock comprising acetic acid to hydrogen and a hydrogenation catalyst at a hydrogenation temperature and a hydrogenation pressure to produce a reaction stream comprising ethanol, ethyl acetate or acetic acid; and exposing the reaction stream to a condensation catalyst at a condensation temperature and a condensation pressure to produce aromatic hydrocarbons.

Another aspect of the invention is a method of converting lactic acid to aromatic hydrocarbons, the method comprising exposing a feedstock comprising lactic acid to hydrogen and a hydrogenation catalyst at a hydrogenation temperature and a hydrogenation pressure to produce a reaction stream comprising propylene glycol, propyl lactate, proprionic acid, propyl propionate, 2-propanol, 1-propanol; and exposing the reaction stream to a condensation catalyst at a condensation temperature and a condensation pressure to produce aromatic hydrocarbons.

DETAILED DESCRIPTION OF THE INVENTION

Figure 1:
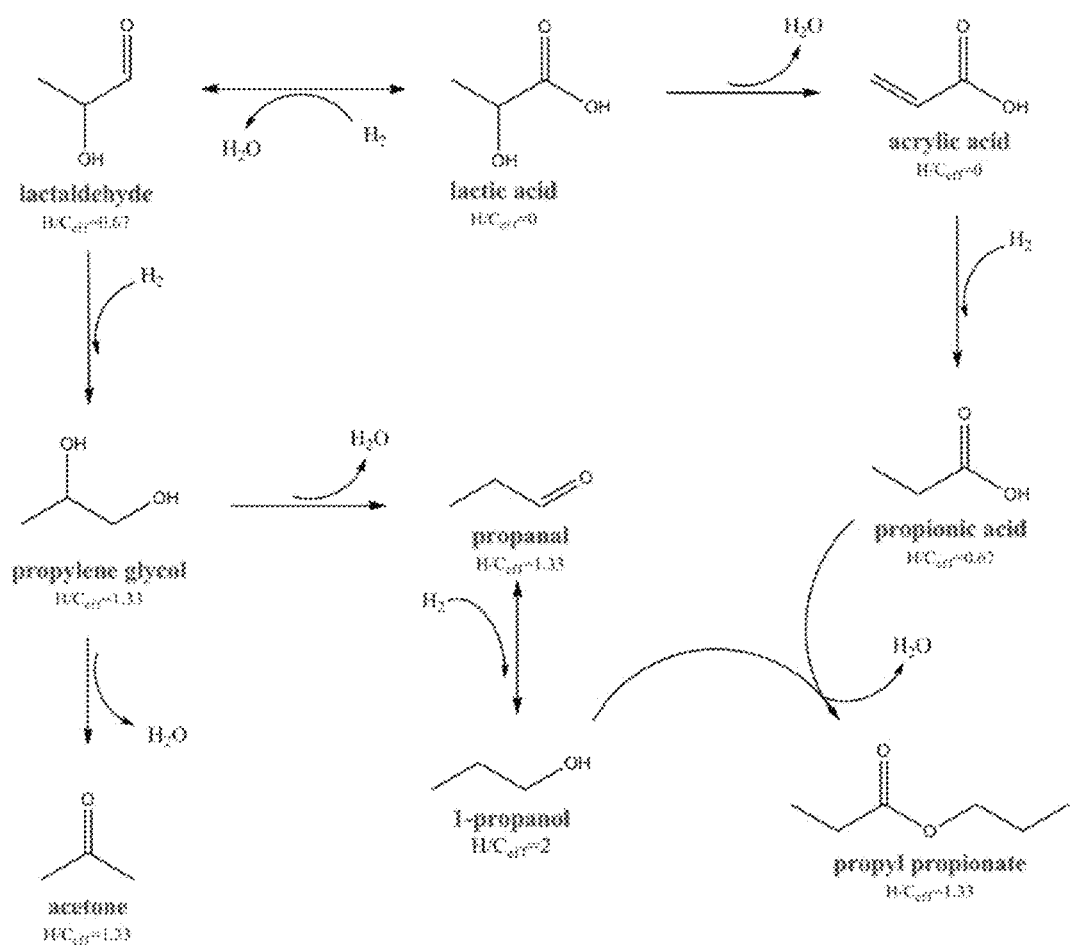
FIG. 1 is an illustration of the chemistry involved in one aspect of the present invention using lactic acid as the feedstock.

The present invention relates to methods, reactor systems, and catalysts for producing aromatic hydrocarbons at high yields. The invention also includes methods of using catalysts to increase the yield of aromatic hydrocarbons—namely benzene, toluene, xylene (dimethylbenzene), ethyl benzene, para xylene, meta xylene, ortho xylene and other $C_9$ aromatics—from carboxylic acid feedstocks.

The method generally involves: (1) a conditioning step which includes exposing a carboxylic acid feedstock to hydrogen and a hydrogenation catalyst at a hydrogenation temperature and a hydrogenation pressure to produce an oxygenate mixture; and (2) exposing the oxygenate mixture to a condensation catalyst at a condensation temperature and a condensation pressure to produce aromatic hydrocarbons. Due to the unique nature of the oxygenate mixture, the resulting yield of aromatic hydrocarbons is greater than those achieved in processes not involving a conditioning step.

As used herein, the term "oxygenates" refers to, without limitation molecules of the general formula $C_L H_M O_N$ where L, M, and N are greater than or equal to one. In certain embodiments L is between 1 and 6, including L equal to 1, 2, 3, 4, 5, or 6. In certain embodiments M is between 1 and 2L+2, including L equal to 1, 2, 3, 4, 5, 6, 7, 8, 9, 10, 11, 12, 13, or 14. In certain embodiments N is between 1 and 6, including N equal to 1, 2, 3, 4, 5, or 6. Oxygenates also includes, without limitation, alcohols, carboxylic acids, esters, aldehydes, or ketones.

As used herein, the term "alcohols" refers to, without limitation, aliphatic alcohols. In certain embodiments, the alcohols have the general formula $C_n H_{2n+2} O_1$, but alcohols also include molecules having two or more hydroxyl moieties such as glycols, glycerols, polyhydric alcohols, and/or sugar alcohols. A person of ordinary skill in the art will be able to determine the formula for alcohols having two or more hydroxyl moieties. Alcohols suitable for use in feedstocks in accord with the invention include $C_1$ to $C_6$ alcohols, including primary, secondary, tertiary, or polyhydric alcohols. Examples of alcohols suitable for use in accordance with this invention include, without limitation, one or more of methanol, ethanol, n-propanol, iso-propanol, n-butanol, 2-butanol, isobutanol, n-pentanol, n-hexanol, ethylene glycol, propylene glycol, glycerol, erythritol, threitol and sugar alcohols. Tertiary alcohols are used, they should be combined with primary or secondary alcohols.

The term "carboxylic acids" refers to, without limitation, organic acids characterized by the presence of at least one carboxyl group. The general formula of the carboxylic acid is R—COOH, where R is a functional group containing hydrogen; carbon and hydrogen; or carbon, hydrogen, and oxygen. In one embodiment, the carboxylic acid has the formula $C_n H_{2n+1} C(=O)OH$, but carboxylic acids also include molecules having two or more carboxyl moieties. Carboxylic acids may also include other moieties containing oxygen such as carbonyl and/or hydroxyl moieties. A person of ordinary skill in the art will be able to determine the formula for carboxylic acids having two or more moieties containing oxygen. Carboxylic acids suitable for use as feedstocks in accord with the invention include $C_1$ to $C_6$ mono-carboxylic, di-carboxylic acids, tri-carboxylic acids, and may also include, without limitation, oxocarboxylic acids or hydroxycarboxylic acids. Examples of carboxylic acids suitable for use in accordance with this invention include, without limitation, one or more of formic acid, acetic acid, propionic acid, butyric acid, isobutyric acid, valeric acid, isovaleric acid, caproic acid, oxalic acid, malonic acid, succinic acid, glutaric acid, adipic acid, glycolic acid, acrylic acid, lactic acid, pyruvic acid, maleic acid, fumaric acid, glutaconic acid, itaconic acid, muconic acid, and citric acid.

The term "ester" refers to, without limitation, an organic compound with the structure RC(=O)OR', where R and R' can be a variety of hydrocarbon substituents. Esters feature a carboxyl group C(=O)O bonded to two carbon atoms. In one embodiment, the ester has a formula $C_n H_{2n+1} C(=O)OC_{n'} H_{2n'+1}$. Esters may also include other moieties containing oxygen such as carbonyl and/or hydroxyl moieties. A person of ordinary skill in the art will be able to determine the formula for esters having two or more moieties containing oxygen. Esters suitable for use as feedstocks in accord with the invention include esters having $C_1$ to $C_6$ R and/or $C_1$ to $C_6$ R' substituents, and may also include, without limitation, hydroxyesters, oxoesters. Examples of esters suitable for use in accordance with this invention include, without limitation, one or more of methyl formate, methyl acetate, methyl propanoate, methyl butanoate, methyl pentanoate, methyl hexanoate, ethyl formate, ethyl acetate, ethyl propanoate, ethyl butanoate, ethyl pentanoate, ethyl hexanoate, propyl formate, propyl acetate, propyl propanoate, propyl butanoate, propyl pentanoate, propyl hexanoate, butyl formate, butyl acetate, butyl propanoate, butyl butanoate, butyl pentanoate, butyl hexanoate, pentyl formate, pentyl acetate, pentyl propanoate, pentyl butanoate, pentyl pentanoate, pentyl hexanoate, hexyl formate, hexyl acetate, hexyl propanoate, hexyl butanoate, hexyl pentanoate, hexyl hexanoate, hydroxy esters thereof, and oxoesters thereof.

The term "aldehyde" refers to, without limitation, an organic compound with the structure RC(=O)H, where R can be a variety of hydrocarbon substituents. Aldehydes feature a carbonyl group (C=O) bonded to one other carbon atom and a hydrogen atom. In one embodiment, the aldehyde has a formula $C_n H_{2n+1} C(=O)H$, but aldehydes also include molecules having two or more carbonyl moieties. Aldehydes may also include other moieties containing oxygen such a hydroxyl moiety. A person of ordinary skill in the art will be able to determine the formula for aldehydes having two or more moieties containing oxygen. Aldehydes suitable for use as feedstocks in accord with the invention include $C_1$ to $C_6$ aldehydes, and may include, without limitation, dialdehydes, hydroxyaldehydes, or ketoaldehydes. Examples of ketones suitable for use in accordance with this invention include, without limitation, one or more of formaldehyde, acetaldehyde, propanal, butanal, pentanal, hexanal, 1,3-propandial, 1,4-butandial, 1,5-pentandial, 1,6-hexandial, 2-oxopropanal, 2-oxobutanal, 3-oxopropanal, 2-oxopentanal, 3-oxopentanal, 4-oxopentanal, 2-oxohexanal, 3-oxohexanal, 4-oxohexanal, 5-oxohexanol, 2-hydroxypropanal, 2-hydroxybutanal, 3-hydroxypropanal, 2-hydroxypentanal, 3-hydroxypentanal, 4-hydroxypentanal, 2-hydroxyhexanal, 3-hydroxyhexanal, 4-hydroxyhexanal, and 5-hydroxyhexanol.

The term "ketone" refers to, without limitation, an organic compound with the structure RC(=O)R', where R and R' can be a variety of hydrocarbon substituents. Ketones feature a carbonyl group (C=O) bonded to two other carbon atoms. In one embodiment, the ketone has a formula $C_nH_{2n+1}C(=O)C_nH_{2n'+1}$, but ketones also include molecules having two or more carbonyl moieties. Ketones may also include other moieties containing oxygen such a hydroxyl moiety. A person of ordinary skill in the art will be able to determine the formula for ketones having two or more moieties containing oxygen. Ketones suitable for use as feedstocks in accord with the invention include $C_1$ to $C_6$ ketones, whether symmetric or asymmetric, and may include, without limitation, hydroxyketones or diketones. Examples of ketones suitable for use in accordance with this invention include, without limitation, one or more of acetone, propanone, 2-oxopropanal, butanone, butane-2,3-dione, 3-hydroxybutan-2-one, pentanone, cyclopentanone, pentane-2,3-dione, pentane-2,4-dione, and hexanone.

The term "aromatic hydrocarbons" refers to, without limitation, aromatic hydrocarbons in either an unsubstituted (phenyl), mono-substituted or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. In one embodiment, at least one of the substituted groups include a branched $C_{3-12}$ alkyl, a straight chain $C_{1-12}$ alkyl, a branched $C_{3-12}$ alkylene, a straight chain $C_{2-12}$ alkylene, a phenyl or a combination thereof. In yet another embodiment, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various aromatic hydrocarbons include, without limitation, benzene, toluene, xylene (dimethylbenzene), ethyl benzene, para xylene, meta xylene, ortho xylene, $C_9$ aromatics.

The carboxylic acids may originate from any source, but are preferably derived from biomass. As used herein, the term "biomass" refers to, without limitation, organic materials produced by plants (such as leaves, roots, seeds and stalks), and microbial and animal metabolic wastes. Common sources of biomass include: (1) agricultural wastes, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; and (4) energy crops, such as poplars, willows, pine, switch grass, alfalfa, prairie bluestream, corn, soybean, and the like. The term also refers to the primary building blocks of the above, namely, saccharides, lignin, cellulosics, hemicellulose and starches, among others.

Biomass-derived carboxylic acids may be produced by any known method. Such methods include, without limitation, fermentation, hydrogenolyis of sugars, hydrolysis of triglycerides, pyrolysis, aqueous phase reforming or other catalytic conversion processes. In one embodiment, the carboxylic acids are produced using catalytic reforming technologies, such as the BioForming® technology developed by Virent, Inc. (Madison, Wis.), and described in U.S. Pat. No. 7,767,867 (Cortright), U.S. Pat. No. 7,898,664 (Cortright), U.S. Pat. No. 8,053,615 (Cortright et al.), U.S. Pat. No. 8,017,818 (Cortright et al.), and U.S. Pat. No. 7,977,517 (Cortright et al.), all of which are incorporated herein by reference.

In another embodiment, the carboxylic acids are produced using a fermentation process. Fermentation processes to produce carboxylic acids from biomass are well known in the art, and generally include (1) pretreating the biomass under well-known conditions to loosen lignin and hemicellulosic material from cellulosic material, (2) breaking down the cellulosic material into fermentable saccharide material by the action of a cellulase enzyme, and (3) fermentation of the saccharide material, typically by the action of a fermenting organism, such as yeast or one of various bactium useful in producing carboxylic acids. For example, the bacteria may be any one of the lactic acid fermenting bacteria from the genus *Lactobacillus* or *Streptococcus*, or acetic acid fermenting bacteria from the genus *Acetobacter, Clostridium* or *Acetobacterium*.

In one embodiment, the conversion method of the present invention is integrated with a fermentation process, wherein the fermentation process produces the carboxylic acid used as the feedstock. The term "integrated" is intended to mean that the carboxylic acid is produced at a fermentation facility or within a fermentation process that is linked to the conversion facility (which performs the conversion process described herein). Preferably, in order to minimize production costs, the fermentation process is in close enough proximity to the conversion facility, or includes appropriate conduits for transferring the produced carboxylic acid to the conversion facility, thereby not requiring the carboxylic acid to be shipped. In particular embodiments, the fermentation stream produced in the fermentation facility is directly transferred to the conversion facility, generally with removal of solids from the raw stream (generally by filtration or settling) before contact of the stream with the catalyst.

In some embodiments, the fermentation process is performed in an autonomous fermentation facility, i.e., where saccharides, produced elsewhere, are loaded into the fermenting system to produce carboxylic acid. In other embodiments, the fermentation process is part of a larger biomass reactor facility, i.e., where biomass is decomposed into fermentable saccharides, which are then processed in a fermentation zone.

In other embodiments, the carboxylic acid is produced from a more direct sugar source, such as a plant-based source of sugars, such as sugar cane or a grain starch (such as corn starch). Lactic acid and acetic acid production via corn starch currently represent some of the largest commercial production methods of carboxylic acid. Integration of the instant conversion process with any of these large scale acid production methods is contemplated herein.

In one embodiment, the carboxylic acid is produced from $CO_x$ molecules, carbon monoxide and/or carbon dioxide, and hydrogen. In certain embodiments the $CO_x$ and hydrogen are a synthesis gas derived from biomass, natural gas, coal, or petroleum. Methods for preparing $CO_x$ molecules and/or hydrogen include, without limitation, fermentation, gasification, combustion, steam reforming, aqueous phase reforming, or the production as a byproduct of the hydrogenation or condensation methods described herein, or combinations thereof. The $CO_x$ molecules and hydrogen can be catalytically reacted to produce carboxylic acids by alcohol synthesis, Fischer-Tropsch synthesis, partial oxidation, or combinations thereof.

In one embodiment, the carboxylic acid is produced from hydrocarbons and oxygen. In certain embodiments the hydrocarbons are alkanes derived from biomass, natural gas, coal, or petroleum. Methods for preparing hydrocarbons include, without limitation, pyrolysis, aqueous phase reforming, liquefaction, or the production as a byproduct of the hydrogenation or condensation methods described herein. The hydrocarbons can be catalytically reacted to produce carboxylic acids by methods including, without limitation, partial oxidation or other oxidative process.

Surprisingly, aromatic hydrocarbon yield can be increased by conditioning the carboxylic acid feedstocks to provide an oxygenate mixture having an $H:C_{eff}$ ratio of between 0.8 and 1.8, between 1.0 and 1.8, between 1.05 and 1.75, between 1.1 and 1.7, between 1.15 and 1.65, or between 1.2 and 1.6. In one embodiment, the oxygenate mixture has a hydrogen to carbon effective ratio of less than 1.8, 1.75, 1.7, 1.65, 1.6, 1.55, 1.5, 1.45 or 1.4. In another embodiment, the oxygenate component has a hydrogen to carbon effective ratio of greater than 0.8, 0.85, 0.9, 0.95, 1.0, 1.05, 1.1, 1.15, 1.2, 1.25, 1.3, 1.35, 1.4, 1.45, or 1.5. The $H:C_{eff}$ ratio applies both to individual components and to mixtures of components, but is not valid for components which contain atoms other than carbon, hydrogen, and oxygen. For mixtures, there will be a number of different components with different $H:C_{eff}$ ratios. To calculate the $H:C_{eff}$ ratio for the mixture, the carbon, hydrogen, and oxygen atoms are summed over all components exclusive of water and molecular hydrogen.

Without being bound to any particular theory, the inventors believe that hydrogen atoms, made available through the conversion of relatively hydrogen-deficient carboxylic acids to alcohols, esters, ketones and aldehydes, allows reaction pathways to be exploited across the condensation catalyst that are not feasible for an isolated carboxylic acid feedstock. These reaction pathways include reactions that can directly lead to olefin intermediates such as dehydration of alcohols. Additional olefin intermediates may be indirectly generated through the release and transfer of hydrogen as aromatics are formed and the hydrogen released by the formation of the aromatics is transferred to unsaturated oxygenates such as esters, ketones, aldehydes, and carboxylic acids. As used herein, oxygenates capable of reacting with hydrogen in this manner are termed "hydrogen acceptors". It is believed that carbonyls, carboxylic acids, esters, cyclic ethers, diols, polyols, furans and other oxygenates characterized by having a $H:C_{eff}$ ratio of less than 2 are capable of being hydrogen acceptors, either directly or following other reactions (such as dehydration), which have converted the components to hydrogen acceptors. After accepting hydrogen, the hydrogen acceptors may be converted into species that readily dehydrate to form olefins or may be capable of accepting further hydrogen. It is notable that carboxylic acids, in isolation, exhibit low reactivity across the condensation catalyst and evolve significant amounts of carbon dioxide for those reactions that do occur (N. Y. Chen, D. E. Walsh and L. R. Koeing, Chapter 24: Fluidized-Bed Upgrading of Wood Pyrolysis Liquids and Related Compounds, ACS Symposium Series; Amer. Chem. Soc., Washington D.C. 1988). In contrast, when reacted in the presence of other oxygenates such as alcohols, carboxylic acids readily react to form aromatics. This illustrates that only a portion of a carboxylic acid feed needs to be converted to more hydrogen rich oxygenates to facilitate the overall conversion of the carboxylic acid feedstock.

Figure 2:
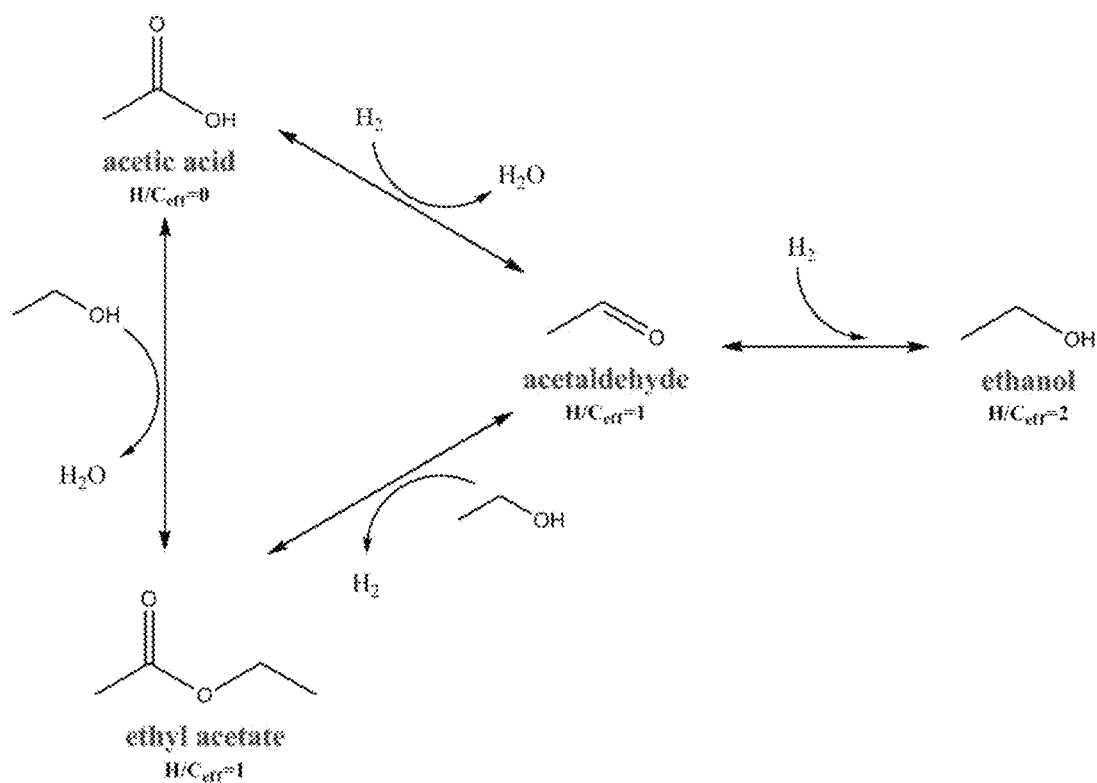
FIG. 2 is an illustration of the chemistry involved in one aspect of the present invention using acetic acid as the feedstock.
Figure 3:
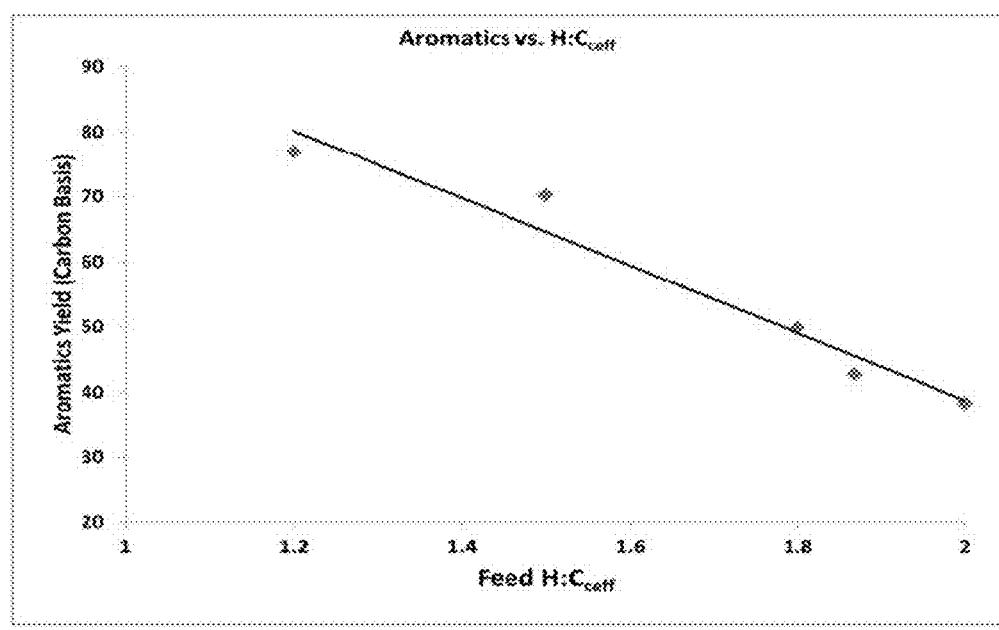
FIG. 3 is a chart illustrating the relationship between the feed hydrogen-to-carbon effective ratio and the aromatic product yield after conversion across a ZSM-5 catalyst in accordance with the present invention.

In one embodiment, the carboxylic acid is acetic acid. As illustrated in FIG. 2, the oxygenates produced from acetic acid generally include acetaldehyde, ethanol and ethyl acetate. Upon reaction, other primary carboxylic acids will produce equivalent products corresponding to the carbon number of the carboxylic acid. The specific products depend on various factors including the composition of the carboxylic acid feedstock, reaction temperature, reaction pressure, carboxylic acid concentration, the reactivity of the catalyst, and the flow rate of the carboxylic acid feedstock as it affects the space velocity (the mass/volume of reactant per unit of catalyst per unit of time).

For illustration purposes, the $H:C_{eff}$ ratio of various carboxylic acids is shown in Table 1 below.

TABLE 1

$H:C_{eff}$ Ratio of Select Carboxylic Acids:

| Carboxylic Acid | $H:C_{eff}$ |
|---|---|
| Formic Acid | −2.00 |
| Acetic Acid | 0.00 |
| Propionic Acid | 0.67 |
| Butyric Acid | 1.00 |
| Isobutyric Acid | 1.00 |
| Valeric Acid | 1.20 |
| Isovaleric acid | 1.20 |
| Caproic acid | 1.33 |
| Oxalic Acid | −3.00 |
| Malonic Acid | −1.33 |
| Succinic Acid | −0.50 |
| Glutaric Acid | 0.00 |
| Adipic Acid | 0.33 |
| Glycolic Acid | −1.00 |
| Acrylic Acid | 0.00 |
| Lactic acid | 0.00 |
| Pyruvic Acid | −0.67 |
| Maleic Acid | −1.00 |
| Fumaric Acid | −1.00 |
| Glutaconic Acid | −0.40 |
| Muconic Acid | −0.33 |
| Citric Acid | −1.00 |

Paraffins generally have a $H:C_{eff}$ ratio greater than 2, while alkyl mono-aromatic compounds generally have a $H:C_{eff}$ ratio between 1 and 2, as shown in Tables 2 and 3 below.

TABLE 2

$H:C_{eff}$ Ratio of Paraffins

| Paraffins | $H:C_{eff}$ |
|---|---|
| $C_1$ | 4 |
| $C_2$ | 3 |
| $C_3$ | 2.67 |
| $C_4$ | 2.5 |
| $C_5$ | 2.4 |
| $C_6$ | 2.33 |
| $C_7$ | 2.29 |
| $C_8$ | 2.25 |
| $C_9$ | 2.22 |
| ↓ | ↓ |
| $C_\infty$ | 2 |

TABLE 3

H:$C_{eff}$ Ratio of Alkyl Substituted Mono-Aromatics

| Aromatic | H:$C_{eff}$ |
|---|---|
| Benzene | 1.0 |
| Toluene | 1.14 |
| Xylene | 1.25 |
| $C_9$ | 1.33 |
| ↓ | ↓ |
| $C_\infty$ | 2 |

As indicated above, the H:$C_{eff}$ ratio of the reactants impacts the H:$C_{eff}$ ratio of the reaction products. When the hydrogen acceptors are passed as reactants over a condensation catalyst, an improved aromatic hydrocarbon yield is realized, relative to the yield realized when the reactants are carboxylic acids alone. The H:$C_{eff}$ ratio of the esters, aldehydes and ketones that may be formed by hydrogenation of carboxylic acids is between zero and 2 as shown in Tables 4 and 5 below.

TABLE 4

H:$C_{eff}$ Ratio of Select Esters

| Esters | H:$C_{eff}$ |
|---|---|
| Methyl Formate | 0.00 |
| Methyl Acetate | 0.67 |
| Ethyl Formate | 0.67 |
| Ethyl Acetate | 1.00 |
| Propyl Propanoate | 1.33 |
| Ethyl Lactate | 0.80 |
| Propyl Lactate | 1.00 |

TABLE 5

H:$C_{eff}$ Ratio of Aldehydes and Ketones

| Aldehydes or Ketone carbon number | H:$C_{eff}$ |
|---|---|
| $C_1$ | 0 |
| $C_2$ | 1.0 |
| $C_3$ | 1.33 |
| $C_4$ | 1.5 |
| $C_5$ | 1.6 |
| $C_6$ | 1.67 |
| $C_7$ | 1.71 |
| $C_8$ | 1.75 |
| $C_9$ | 1.78 |
| ↓ | ↓ |
| $C_\infty$ | 2 |

The H:$C_{eff}$ ratio of ethanol (and of all alkanols) is 2, as shown in Table 6 below.

TABLE 6

H:$C_{eff}$ Ratio of Alcohols

| Alcohol (by number of carbon atoms) | H:$C_{eff}$ |
|---|---|
| $C_1$ | 2 |
| $C_2$ | 2 |
| $C_3$ | 2 |
| $C_4$ | 2 |
| $C_5$ | 2 |
| $C_6$ | 2 |
| $C_7$ | 2 |
| $C_8$ | 2 |
| $C_9$ | 2 |
| ↓ | ↓ |
| $C_\infty$ | 2 |

Other species of interest include carbon dioxide ($CO_2$) with a H:$C_{eff}$ ratio of −4, carbon monoxide (CO) with a H:$C_{eff}$ ratio of −2, and carbon (C) with a H:$C_{eff}$ ratio of 0. Carbonaceous residue, or coke, that may accumulate on catalyst or other surfaces exhibits a range of H:$C_{eff}$ ratios, depending on the amount of residual hydrogen and oxygen within the coke.

In accordance with the invention, the process for converting carboxylic acids to hydrocarbons can be a two-step process (in which the hydrogenation catalyst and the condensation catalyst can be separate catalysts) or a one-step process (in which the hydrogenation catalyst and the condensation catalyst can be one multi-functional catalyst). When separate catalysts are provided, they may be present in separate vessels, in separate beds within a single vessel, in alternating layers in a single bed of catalyst, or physically mixed within the same bed.

The general two-step process is as follows. A carboxylic acid feedstock is first passed into contact with hydrogen and a hydrogenation catalyst in a reactor at a hydrogenation temperature and a hydrogenation pressure, thereby producing a mixture of oxygenates. The carboxylic acid feedstock may be an essentially pure carboxylic acid stream or, alternatively, the carboxylic acid feedstock may be mixed with water and/or an alcohol to create a solution wherein the carboxylic acid concentration is greater than 1%, or greater than 5%, or greater than 10%, or greater than 20%, or greater than 30%, or greater than 40%, or greater than 50%.

The hydrogenation catalyst generally includes Fe, Ru, Co, Pt, Pd, Ni, Re, Cu, and alloys or combinations thereof, either alone or with promoters such as Ag, Au, Cr, Zn, Mn, Mg, Ca, Cr, Sn, Bi, Mo, W, B, P, and alloys or combinations thereof. The hydrogenation catalyst may also include any one of several supports, depending on the desired functionality of the catalyst. Supports may include carbon, silica, alumina, zirconia, titania, vanadia, ceria, silica-aluminate, zeolite, kieselguhr, hydroxyapatite, zinc oxide, magnesium oxide, chromia, and mixtures thereof.

In general, the hydrogenation reaction is carried out at hydrogenation temperatures of between about 80° C. to 350° C., and hydrogenation pressures in the range of about 50 psig to 2000 psig. The hydrogen used in the reaction may include in situ hydrogen generated from other reactions occurring in series or parallel within the reactor, external $H_2$, recycled $H_2$, or a combination thereof.

The extent to which the carboxylic acid feed stock is hydrogenated can be measured by the amount of molecular hydrogen consumed during hydrogenation and may range from 0.05 to 2.0 moles of molecular hydrogen consumed per mole of carboxylic acid groups in the feed. In general, the reaction should be conducted under conditions where the residence time of the carboxylic acid feedstock over the catalyst is appropriate to generate the desired oxygenates. For example, the residence time may be established at a weight hourly space velocity (WHSV) of between 0.01 and 30, or between 0.05 and 10, or between 0.1 and 5.

Desirable levels of hydrogenation depend on the composition of the carboxylic acid feedstock. To enhance the production of aromatics during the condensation, longer chain carboxylic acids must be hydrogenated to a lesser extent than short chain carboxylic acids. For an acetic acid feedstock, greater than 0.8 moles of molecular hydrogen should be consumed per mole carboxylic acid feedstock to the system during hydrogenation, and greater than 1 mole of molecular hydrogen per mole of carboxylic acid is preferred to prevent an excessive coking rate. Lower extent of hydrogenation is required as carbon chain length of the carboxylic acid increases (in the absence of other function groups such as hydroxyls). For a propionic acid feedstock, for example, greater than 0.2 moles of molecular hydrogen should be consumed per mole carboxylic acid feedstock to the system during hydrogenation, and greater than 0.5 mole of molecular hydrogen per mole of carboxylic acid is preferred to prevent an excessive coking rate. For mixed carboxylic acid feedstocks, the overall extent of hydrogenation should be such that the overall H:$C_{eff}$ ratio of the resulting oxygenate stream is less than 1.8, 1.75, 1.7, 1.65, 1.6, 1.55, 1.5, 1.45, or 1.4, and greater than 0.8, 0.85, 0.9, 0.95, 1.0, 1.05, 1.1, 1.15, 1.2, 1.25, 1.3, 1.35, 1.4, 1.45, or 1.5. For example, the overall extent of hydrogenation should be such that the carbon effective ratio is between 0.8 and 1.8, between 1.0 and 1.8, between 1.05 and 1.75, or between 1.1 and 1.7, or between 1.15 and 1.65, or between 1.2 and 1.6. Hydrogenation extent may be controlled by varying the catalyst and operating conditions. Higher temperatures generally lead to lower equilibrium levels of hydrogenation but higher catalyst activity. Higher hydrogen partial pressure generally leads to greater levels of hydrogenation. Other components, such as additional oxygenates, for example alcohols, may be added to the hydrogenation products to ensure that the overall H:$C_{eff}$ ratio of the resulting oxygenate stream is achieved. In addition to the hydrogenation reactions, additional reactions may be supported during the hydrogenation step, including esterification, dehydration, and aldol condensation.

In another embodiment, the hydrogenation of the carboxylic acid feedstock is supplemented by combining the feedstock stream or the oxygenate mixture with additional oxygenates to arrive at a oxygenate mixture having the desired H:Ceff ratio of between 0.8 and 1.8. The additional oxygenates may include without limitation alcohols, esters, aldehydes, or ketones.

The oxygenate mixture, including unreacted carboxylic acids and the hydrogenation products, are then passed in whole or in part into contact with a condensation catalyst in a reactor under conditions of temperature and pressure effective to convert a portion of the oxygenate mixture to aromatic hydrocarbons. In general, the condensation catalyst has one or more acidic materials capable of catalyzing the conversion of the oxygenate mixture components to the desired aromatic hydrocarbons. The condensation catalyst may include, without limitation, aluminosilicates (zeolites), silica-alumina phosphates (SAPO), aluminum phosphates (ALPO), amorphous silica alumina, zirconia, sulfated zirconia, tungstated zirconia, titania, acidic alumina, phosphated alumina, phosphated silica, sulfated carbons, phosphated carbons, heteropolyacids, and combinations thereof. In one embodiment, the catalyst may also include a modifier, such as Ce, Y, Sc, La, P, B, Bi, Li, Na, K, Cs, Mg, Ca, Ba, and combinations thereof. The catalyst may also be modified by the addition of a metal, such as Cu, Ag, Au, Pt, Ni, Fe, Co, Ru, Zn, Cd, Ga, In, Rh, Pd, Ir, Re, Mn, Mg, Cr, Mo, W, Sn, Os, alloys and combinations thereof, to provide metal functionality, and/or oxides of Ti, Zr, V, Nb, Ta, Mo, Cr, W, Mn, Re, Al, Ga, In, Fe, Co, Mg, Ni, Si, Cu, Zn, Sn, P, and combinations thereof. The condensation catalyst may be self-supporting or adhered to any one of the supports further described below, including supports containing carbon, silica, alumina, zirconia, titania, zinc oxide, magnesium oxide, aluminum phosphate, zinc aluminate, vanadia, ceria, heteropolyacids, alloys and mixtures thereof.

Ga, In, Zn, Fe, Mo, Ag, Au, Ni, P, Sc, Y, Ta, and lanthanides may also be exchanged onto zeolites to provide a zeolite catalyst. The term "zeolite" as used herein refers not only to microporous crystalline aluminosilicate but also for microporous crystalline metal-containing aluminosilicate structures, such as galloaluminosilicates and gallosilicates. Metal functionality may be provided by metals such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. Nos. 3,702,886; Re. 29,948 (highly siliceous ZSM-5); U.S. Pat. No. 4,100,262 and U.S. Pat. No. 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. No. 5,019,663 and U.S. Pat. No. 7,022,888, also incorporated herein by reference.

As described in U.S. Pat. No. 7,022,888, the condensation catalyst may be a bifunctional pentasil zeolite catalyst including at least one metallic element from the group of Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, or a modifier from the group of Ga, In, Zn, Fe, Mo, Au, Ag, Y, Sc, Ni, P, Ta, lanthanides, and combinations thereof. The zeolite may be used with reactant streams containing an oxygenated hydrocarbon at a temperature of below 600° C. The zeolite may have ZSM-5, ZSM-8 or ZSM-11 type crystal structure consisting of a large number of 5-membered oxygen-rings, i.e., pentasil rings. The zeolite with ZSM-5 type structure is a particularly preferred catalyst.

The catalyst may optionally contain any binder such as alumina, silica or clay material. The catalyst can be used in the form of pellets, extrudates and particles of different shapes and sizes. In one aspect, the condensation catalyst is ZSM-5 or beta zeolite.

In general, the condensation temperature is between about 250° C. and 550° C., and in some embodiments between about 300° C. and 500° C. or between about 320° C. and 480° C. The condensation pressure ranges from below atmospheric pressure up to about 1000 psig, and in some embodiments from about atmospheric pressure to about 700 psig or from about 10 psig to about 500 psig. In general, the reaction should be conducted under conditions where the residence time of the hydrogenation products over the condensation catalyst is appropriate to generate the desired aromatic hydrocarbons. For example, the residence time may be established at a weight hourly space velocity (WHSV) of between 0.01 and 30, or between 0.05 and 10, or between 0.1 and 5, or between 1.0 and 4.

Excluding molecular hydrogen ($H_2$), the overall $H:C_{eff}$ ratio of the oxygenate mixture is generally greater than 0.8 and less than 1.8, resulting in an increased yield of aromatics, and an improvement over traditional methods of converting carboxylic acids to aromatic hydrocarbons. When the hydrogenation (conditioning) and condensation are complete, more than 40%, or 45%, or 50%, or 60%, or 70%, or 75%, of the carbon in the carboxylic acid feedstock is contained within the aromatic hydrocarbon product.

The present invention may also be practiced as a one-step process in which the hydrogenation catalyst and the condensation catalyst is a multi-functional catalyst. In this approach, carboxylic acids are converted to hydrocarbons employing a multi-functional catalyst having one or more materials capable of catalyzing both the hydrogenation and condensation reactions. The multi-functional catalyst may include any of the elements suitable for separate hydrogenation and condensation catalysts discussed above. One particularly useful catalyst is copper loaded onto silica-bound ZSM-5. In this single-step embodiment, the hydrogenation reaction and the condensation reactions occur in the same reaction vessel under conditions of temperature and pressure as described above and which are suitable for both the hydrogenation and condensation reactions to proceed.

In some embodiments, the oxygenate mixture is separated to provide one or more streams which are directed to the conversion reactor and one or more streams which are not directly fed into the conversion reactor. The streams which are not directly fed into the conversion reactor may be removed from the system or recycled to the hydrogenation reactor for further conversion. Means of separation include, without limitation, separation based on volatility differences between components, extraction, membranes, and ion exchange. In one preferred embodiment, the products of the conditioning step are cooled and a portion of the molecular hydrogen unused in the reaction step is removed as a gas phase product prior to sending the remaining components to the condensation reactor. In another preferred embodiment, the oxygenate mixture is separated by distillation to provide an aldehyde enriched stream which is recycled to the hydrogenation reactor to effect conversion of the aldehydes to alcohols and esters. In yet another preferred embodiment, unreacted carboxylic acids are separated from the product stream and recycled to the hydrogenation reactor to increase the overall carboxylic acid conversion.

In other embodiments, oxygenates other than carboxylic acids may be used in addition to and as a supplement to the carboxylic acid feedstock. Because the carboxylic acids are derived from biomass, the age of the compounds, or fractions containing the compounds, is less than 100 years old, preferably less than 40 years old, more preferably less than 20 years old, as calculated from the carbon 14 concentration of the component.

EXAMPLE

To demonstrate the advantage of using a mixture of oxygenates, experiments using ethanol, acetic acid, and both ethanol and acetic acid were performed.

In the experiment, two Inconel reactors aligned in series were loaded with the catalyst described in Example 8 of U.S. Patent Application 2013/0131411. Each reactor had an internal diameter of 0.87 inches with an Inconel thermowell with an OD of 0.1875 inches running through the center of the reactor. The catalyst was loaded to a depth of 11.5 inches, accounting for 72 g of catalyst per reactor. The catalysts were heated up at atmospheric pressure flowing approximately 200 ml/min $N_2$ across the catalyst while ramping the temperatures from 25° C. to 375° C. in 2 hours.

Once at temperature, the reactors were pressurized with $N_2$ to 200 psig. A compressor was turned on to provide a gas recirculation stream across these two reactors at a rate of approximately 1300 sccm. At this point, a feed mixture having a $H:C_{eff}$ ratio of 2.0 consisting of 80% ethanol and 20% water (by mass) was fed downflow into the first reactor at a rate of 0.63 g/min. Once steady state conditions were achieved, an analysis of reaction products was completed. The gas products were analyzed by means of a gas chromatograph equipped with a flame ionization detector, the aqueous phase products were analyzed for total carbon and with a gas chromatograph equipped with a mass spectrometry detector, and the organic phase components were analyzed using a gas chromatograph equipped with both flame ionization and mass spectrometry detectors. Four separate data points were obtained, and the average-normalized yield (as % of carbon feed) are presented in Table 7 and FIG. 4 below.

Figure 4:
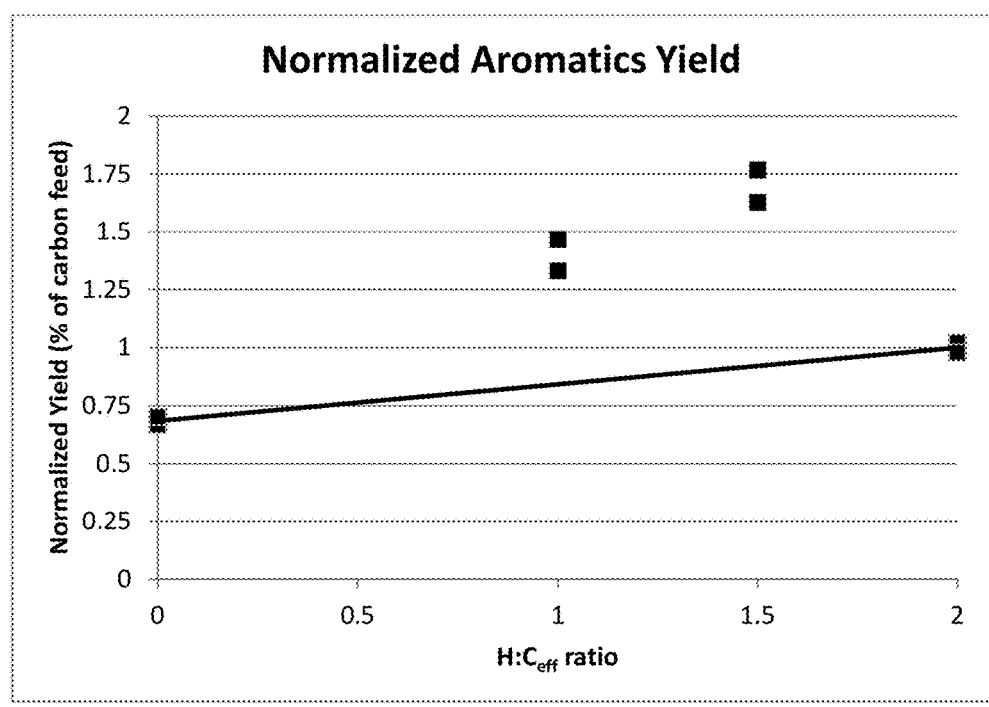
FIG. 4 is a chart illustrating the yield of aromatic hydrocarbons for mixture of acetic acid and ethanol in comparison to acetic acid only and ethanol only.

The experiment was repeated with three separate feeds. The first was a feed mixture having a $H:C_{eff}$ ratio of 0.0 consisting of 80% acetic acid and 20% water (by mass). The second was a feed mixture having a $H:C_{eff}$ ratio of 1.5 consisting of 56% ethanol, 24% acetic acid, and 20% water (by mass). The third was a feed mixture having a $H:C_{eff}$ of 1.0 consisting of 34.7% ethanol, 45.3% acetic acid, and 20% water (by mass). Two separate data points were obtained for each feed, and the results were normalized by the ethanol-only average. The data is presented in Table 7 and FIG. 4 below. Also presented in FIG. 4 is a straight line fit to the ethanol-only and acetic acid-only feeds.

TABLE 7

Aromatic chemical yield as a function of a mixture of ethanol and acetic acid

| Feed | $H:C_{eff}$ Ratio | Aromatics Yield (% of feed Carbon) | Normalized Yield (% of feed Carbon) |
|---|---|---|---|
| Ethanol | 2.0 | 39.9% | 1.00 |
| Ethanol | 2.0 | 40.0% | 1.00 |
| Ethanol | 2.0 | 40.9% | 1.02 |
| Ethanol | 2.0 | 39.2% | 0.98 |
| Acetic Acid | 0.0 | 26.7% | 0.67 |
| Acetic Acid | 0.0 | 27.1% | 0.70 |
| Ethanol/Acetic Acid | 1.5 | 70.7% | 1.77 |
| Ethanol/Acetic Acid | 1.5 | 65.1% | 1.63 |
| Ethanol/Acetic Acid | 1.0 | 58.6% | 1.47 |
| Ethanol/Acetic Acid | 1.0 | 53.2% | 1.33 |

The invention claimed is:

1. A method of converting carboxylic acids to aromatic hydrocarbons, the method comprising:
   (a) partially hydrogenating a feedstock comprising carboxylic acids in the presence of hydrogen and a hydrogenation catalyst at a hydrogenation temperature in the range of 80° C. to 350° C. a hydrogenation pressure in the range of 50 psig to 2000 psig, and a weight hourly space velocity in the range of 0.01 to 30 to produce an oxygenate mixture comprising (1) an unreacted carboxylic acid and (2) at least one member selected from the group consisting of an alcohol, an ester, a ketone, and an aldehyde, wherein the oxygenate mixture has an average H:$C_{eff}$ ratio of between 1.2 and 1.6; and (b) exposing the oxygenate mixture to a condensation catalyst comprising a member selected from the group consisting of aluminosilicates, silica-alumina phosphates, and aluminum phosphates at a condensation temperature and a condensation pressure to produce aromatic hydrocarbons wherein greater than 40% of carbon in the feedstock is contained within the aromatic hydrocarbons.

2. The method of claim 1, wherein a portion of the feedstock is less than 100 years old as calculated from the carbon 14 concentration of the feedstock.

3. The method of claim 1, wherein the feedstock comprises an alkyl-acid or an α-hydroxy acid.

4. The method of claim 1, wherein the carboxylic acid feedstock comprises acetic acid or lactic acid.

5. The method of claim 1, wherein the oxygenate mixture comprises a combination selected from the group consisting of (i) an unreacted carboxylic acid and an alcohol; (ii) an unreacted carboxylic acid and an ester; and (iii) an unreacted carboxylic acid, an alcohol and an ester.

6. The method of claim 5, wherein the oxygenate mixture further comprises an aldehyde, a ketone, or both an aldehyde and a ketone.

7. The method of claim 1, wherein the oxygenate mixture comprises a plurality of molecules having a hydrogen to carbon effective ratio less than 1.6.

8. The method of claim 1, wherein the hydrogenation catalyst comprises a support and a member selected from the group consisting of Fe, Ru, Co, Pt, Pd, Ni, Re, Cu, alloys thereof, and a combination thereof.

9. The method of claim 8, wherein (i) the hydrogenation catalyst further comprises a member selected from the group consisting of Ag, Au, Cr, Zn, Mn, Mg, Ca, Cr, Sn, Bi, Mo, W, B, P, alloys thereof, and a combination thereof, (ii) the support comprises a member selected from group consisting of a carbon, silica, alumina, zirconia, titania, vanadia, ceria, silica-aluminate, zeolite, kieselguhr, hydroxyapatite, zinc oxide, chromia, and mixtures thereof, or both (i) and (ii).

10. The method of claim 9, wherein the support is modified by treating the support with a modifier selected from the group consisting of silanes, alkali compounds, alkali earth compounds, and lanthanides.

11. The method of claim 1, wherein the condensation catalyst comprises a zeolite.

12. The method of claim 11, wherein (i) the condensation catalyst is ZSM-5, (ii) the condensation catalyst is modified by a material selected from the group consisting of phosphorous, gallium, zinc, nickel, tungsten, and mixtures thereof, and (iii) the condensation catalyst is contained within a binder selected from the group consisting of alumina, silica, silica-alumina, titania, zinc aluminate, zirconia, aluminum phosphate, and mixtures thereof, or any combination thereof.

13. The method of claim 1, wherein (i) the condensation pressure ranges from less than atmospheric pressure to about 1000 psig, and (ii) the condensation temperature is between about 250° C. and 550° C., or both (i) and (ii).

14. The method of claim 1, wherein the oxygenate mixture has an average H:$C_{eff}$ ratio of between 1.3 and 1.6.

15. The method of claim 1, wherein greater than 45% of carbon in the feedstock is contained within the aromatic hydrocarbons.

16. A method of converting acetic acid or lactic acid to aromatic hydrocarbons, the method comprising:

(a) partially hydrogenating a feedstock comprising acetic acid in the presence of hydrogen and a hydrogenation catalyst at a hydrogenation temperature in the range of 80° C. to 350° C., a hydrogenation pressure in the range of 50 psig to 2000 psig, and a weight hourly space velocity in the range of 0.01 to 30 to produce a reaction stream, wherein the reaction stream has an average H:$C_{eff}$ ratio of between 1.2 and 1.6 comprising ethanol, ethyl acetate or acetic acid or (b) partially hydrogenating a feedstock comprising lactic acid in the presence of hydrogen and a hydrogenation catalyst at a hydrogenation temperature in the range of 80° C. to 350° C., a hydrogenation pressure in the range of 50 psig to 2000 psig, and a weight hourly space velocity in the range of 0.01 to 30 to produce a reaction stream, wherein the reaction stream has an average H:$C_{eff}$ ratio of between 1.2 and 1.6 comprising propylene glycol, propyl lactate, propionic acid, propyl propionate, 2-propanol, or 1-propanol; and exposing the reaction stream to a condensation catalyst comprising a member selected from the group consisting of aluminosilicates, silica-alumina phosphates, and aluminum phosphates at a condensation temperature and a condensation pressure to produce aromatic hydrocarbons, wherein greater than 40% of carbon in the feedstock is contained within the aromatic hydrocarbons.

* * * * *